US012649702B2

(12) United States Patent
Fichtl et al.

(10) Patent No.: US 12,649,702 B2
(45) Date of Patent: Jun. 9, 2026

(54) PROCESS FOR PRODUCING RENEWABLE MONO-METHYL ALKYLBENZENE PRODUCTS

(71) Applicant: UOP LLC, Des Plaines, IL (US)

(72) Inventors: Geoffrey W. Fichtl, Chicago, IL (US); Phuong T.M. Do, Mount Prospect, IL (US); James T. Wexler, Wheaton, IL (US); Hai Du, Hinsdale, IL (US); Eseoghene Jeroro, Chicago, IL (US); Patrick C. Whitchurch, Elgin, IL (US)

(73) Assignee: UOP LLC, Des Plaines, IL (US)

( * ) Notice: Subject to any disclaimer, the term of this patent is extended or adjusted under 35 U.S.C. 154(b) by 319 days.

(21) Appl. No.: 18/500,166

(22) Filed: Nov. 2, 2023

(65) Prior Publication Data

US 2024/0400474 A1 Dec. 5, 2024

Related U.S. Application Data

(60) Provisional application No. 63/504,881, filed on May 30, 2023.

(51) Int. Cl.
*C07C 2/64* (2006.01)
*C07C 1/213* (2006.01)
(Continued)

(52) U.S. Cl.
CPC .................. *C07C 2/64* (2013.01); *C07C 7/13* (2013.01); *C07C 2523/652* (2013.01);
(Continued)

(58) Field of Classification Search
CPC .. C07C 1/213; C07C 2/64; C07C 4/06; C07C 5/05; C07C 5/222; C07C 5/327;
(Continued)

(56) References Cited

U.S. PATENT DOCUMENTS

| | | | |
|---|---|---|---|
| 4,133,842 | A | 1/1979 | Anderson |
| 6,177,381 | B1 | 1/2001 | Jensen et al. |

(Continued)

FOREIGN PATENT DOCUMENTS

| | | | |
|---|---|---|---|
| EP | 1966357 B1 | 4/2019 |
| JP | S5579327 A | 6/1980 |

(Continued)

OTHER PUBLICATIONS

Roald Brosius et al., Selective Formation of Linear Alkanes from n-Hexadecane Primary Hydrocracking in Shape-Selective MFI Zeolites by Competitive Adsorption of Water, ACS Catal. 2016, 6, 7710-7715.

(Continued)

*Primary Examiner* — In Suk C Bullock
*Assistant Examiner* — Jason Y Chong

(57) ABSTRACT

Processes for producing mono-methyl alkylbenzenes from natural oils are described. The processes includes a linear selective cracking process to crack C14+ chains into C9 to C14 chains which are useful for making linear alkylbenzene for use in detergents and a hydroisomerization step to produce paraffins with mono-methyl branching which can be reacted with benzene to form the mono-methyl alkyl benzenes.

19 Claims, 2 Drawing Sheets

(51) Int. Cl.

| | |
|---|---|
| ***C07C 4/06*** | (2006.01) |
| ***C07C 5/05*** | (2006.01) |
| ***C07C 5/22*** | (2006.01) |
| ***C07C 5/327*** | (2006.01) |
| ***C07C 7/13*** | (2006.01) |

(52) U.S. Cl.
CPC ...... *C07C 2523/84* (2013.01); *C07C 2529/85* (2013.01); *C07C 2601/16* (2017.05)

(58) Field of Classification Search
CPC ....... C07C 7/00; C07C 7/13; C07C 2523/652; C07C 2523/84; C07C 2529/85; C07C 2601/16
See application file for complete search history.

(56) References Cited

U.S. PATENT DOCUMENTS

| | | | |
|---|---|---|---|
| 6,187,981 | B1 * | 2/2001 | Marinangeli ......... C07C 15/107 585/323 |
| 6,187,987 | B1 * | 2/2001 | Chin ...................... C10G 67/02 585/818 |
| 8,865,956 | B2 | 10/2014 | Anumakonda et al. |
| 9,079,814 | B2 | 7/2015 | Frey et al. |
| 10,894,753 | B1 | 1/2021 | Hickman et al. |
| 2006/0247481 | A1 | 11/2006 | Kulprathipanja et al. |
| 2008/0194895 | A1 | 8/2008 | Sohn et al. |
| 2009/0158637 | A1 | 6/2009 | McCall et al. |
| 2013/0079570 | A1 | 3/2013 | Anumakonda et al. |
| 2013/0079573 | A1 | 3/2013 | Bozzano et al. |
| 2013/0253243 | A1 | 9/2013 | Bozzano et al. |
| 2013/0317267 | A1 | 11/2013 | Anumakonda et al. |
| 2013/0338410 | A1 | 12/2013 | Wang et al. |
| 2014/0364355 | A1 | 12/2014 | Frey et al. |
| 2015/0361012 | A1 | 12/2015 | Sohn et al. |
| 2016/0068453 | A1 | 3/2016 | Fichtl et al. |
| 2016/0289139 | A1 | 10/2016 | Baird et al. |
| 2017/0029347 | A1 | 2/2017 | Ellig et al. |
| 2018/0179124 | A1 | 6/2018 | Siedler et al. |
| 2022/0056351 | A1 | 2/2022 | Karvo et al. |
| 2022/0298425 | A1 | 9/2022 | Rämö et al. |
| 2024/0400477 | A1 | 12/2024 | Do et al. |

FOREIGN PATENT DOCUMENTS

| | | | |
|---|---|---|---|
| JP | 2002060760 | A | 2/2002 |
| JP | 2009518534 | A | 5/2009 |
| JP | 2014526552 | A | 10/2014 |
| WO | 2008013519 | A2 | 1/2008 |
| WO | 2014003906 | A1 | 1/2014 |

OTHER PUBLICATIONS

Extended European Search report from European application No. EP23210889.4, mailed on Jun. 3, 2024.
Extended European Search report from corresponding European application No. EP23210890.2, mailed on Jun. 3, 2024.
Extended European Search report from European application No. EP23211561.8, mailed on May 10, 2024.
Extended European Search report from European application No. EP23211836.4, mailed on Mar. 20, 2024.

* cited by examiner

PROCESS FOR PRODUCING RENEWABLE MONO-METHYL ALKYLBENZENE PRODUCTS

RELATED APPLICATIONS

This application claims priority to U.S. Provisional Patent Application Ser. No. 63/504,881, filed on May 30, 2023, the entirety of which is incorporated herein by reference.

BACKGROUND

Linear alkylbenzenes are organic compounds with the formula $C_6H_5C_nH_{2n+1}$. While the alkyl carbon number, "n" can have any practical value, detergent manufacturers desire that alkylbenzenes have alkyl carbon number in the range of 9 to 16 and preferably in the range of 9 to 14. These specific ranges are often required when the alkylbenzenes are used as intermediates in the production of surfactants for detergents. The alkyl carbon number in the range of 9 to 14 falls in line with the specifications of the detergents industry.

Because the surfactants created from alkylbenzenes are biodegradable, the production of alkylbenzenes has grown rapidly since their initial uses in detergent production in the 1960s. The linearity of the paraffin chain in the alkylbenzenes is key to the material's biodegradability and effectiveness as a detergent. A major factor in the final linearity of the alkylbenzenes is the linearity of the paraffin component.

While detergents made utilizing alkylbenzene-based surfactants are biodegradable, previous processes for creating alkylbenzenes are not based on renewable sources. Specifically, alkylbenzenes are currently produced from kerosene refined from crude extracted from the earth. Due to the growing environmental prejudice against fossil fuel extraction and economic concerns over exhausting fossil fuel deposits, there may be support for using an alternate source for biodegradable surfactants in detergents and in other industries.

Some detergent manufacturers serve a specialty market based on alkylbenzenes enriched in mono-methyl alkyl benzenes (MMAB) relative to more typical linear alkyl benzenes (LAB).

Accordingly, it is desirable to provide MMAB that are made from biorenewable sources instead of being extracted from the earth. Further, it is desirable to provide renewable linear alkylbenzenes from vegetable, animal, nut, and/or seed oils to reduce the carbon intensity relative to fossil-based sources of mono-methyl paraffins.

DETAILED DESCRIPTION

Figure 1:
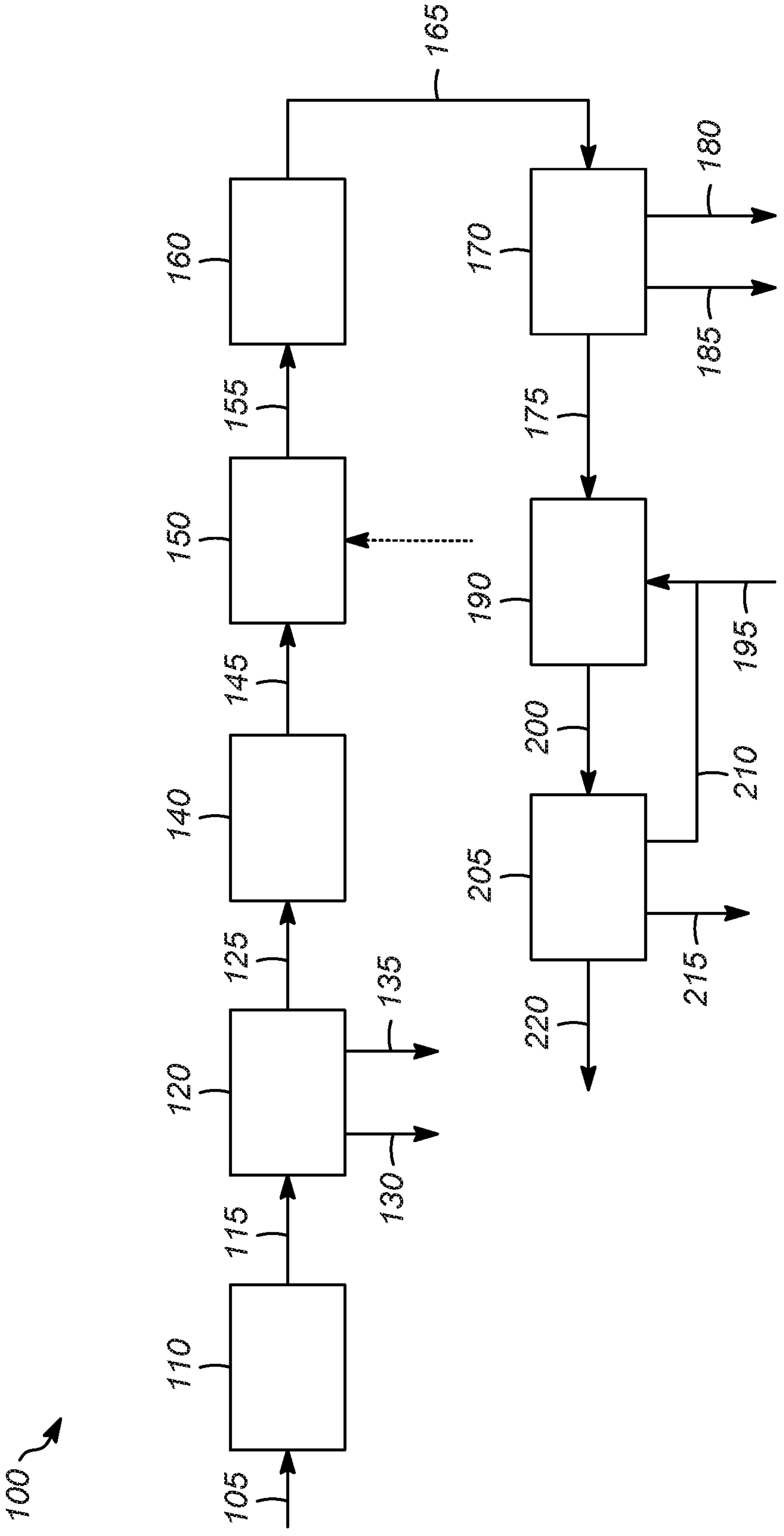
FIG. 1 is a schematic view of one embodiment of a process for producing mono-methyl alkyl benzenes according to the present invention.

The present invention relates to methods for producing a stream enriched in mono-methyl alkylbenzenes from. natural oils, such as vegetable, animal, nut, and/or seed oils, and triglyceride-containing oils. The method provides a stream enriched in mono-methyl paraffins relative to normal paraffins which can be used to produce the mono-methyl alkyl benzenes.

Normal paraffins are generated via deoxygenation and hydrogenation of triglyceride feeds, such as palm kernel oil (PKO), and other plant or animal based oils. The deoxygenation and hydrogenation takes place in the first step of the process by contacting the natural oil feed with a catalyst and hydrogen at elevated temperature and pressure. Some plant based oils, such as PKO or coconut, already have carbon chains that naturally fall in the C9 to C14 range typical in detergent applications. Longer chains can undergo selective hydrocracking to enrich the normal paraffin product of deoxygenation/hydrogenation in normal paraffins with carbon numbers of 9 to 14. From there, normal paraffins can be selectively lightly isomerized in a hydroisomerization step to create a portion of paraffins with mono-methyl branching. The mixture of paraffins can be further enriched in mono-methyl branched paraffins by processing through an adsorption separation system, and raffinate could be recycled to hydroisomerization to further make mono-methyl branched paraffins. The adsorption separation process for a large scale process may use a simulated moving bed design for continuous separation of components in the mixture. The simulated moving bed process is described in U.S. Pat. No. 2,985,589, for example. ZSM and X type zeolites have been used widely in absorption separation systems, as mentioned in U.S. Pat. No. 6,225,518. Suitable adsorbents for the adsorbent system, include but are not limited to, a ZSM or a type X zeolite, such as ZSM-5 or 13X zeolites.

The stream enriched in mono-methyl paraffins is processed through contaminant removal, dehydrogenation, selective hydrogenation, and alkylation to produce the MMAB product. The hydroisomerization step is controlled by proper selection of the catalyst and operating conditions to favor the light branching required to selectively produce mono-methyl branch paraffins rather than paraffins with higher degrees of branching or branching in the wrong position. For feeds with inherent carbon chains longer than 9-14, the linear selective cracking step involved controlling the catalyst and operating condition to enhance the yield of chains in the 9-14 carbon number range.

Natural oils are not based on kerosene or other fossil fuels. Natural oils include those derived from plant or algal material, animal fats, nut and/or seed oils, and triglyceride-containing oils, and are often referred to as renewable oils. Natural oils typically comprise triglycerides, free fatty acids, or combinations thereof. Natural oils include, but are not limited to, *Arachis* oil (peanut oil; groundnut oil), Babassu oil, Coconut oil, Cottonseed oil, Grapeseed oil, Maize oil (corn oil), Mustard seed oil, Palm kernel oil, Palm oil, Palm olein (the liquid fraction derived from the fractionation of palm oil), Palm stearin (the high-melting fraction derived from the fractionation of palm oil), Rapeseed oil, Rapeseed oil—low erucic acid (low erucic acid turnip rape oil; low erucic acid colza oil; canola oil), Safflower seed oil (safflower oil; 3arthamus oil; kurdee oil), Safflower seed oil—high oleic acid (high oleic acid safflower oil; high oleic acid 3arthamus oil; high oleic acid kurdee oil), Sesame seed oil (sesame oil; gingelly oil; benne oil; ben oil; till oil; tillie oil), Soya bean oil (soybean oil), Sunflower seed oil (sunflower oil), and Sunflower seed oil—high oleic acid (high oleic acid sunflower oil).

The methods for making mono-methyl alkylbenzenes from natural oils according to the present invention involve the deoxygenation of the natural oils to form paraffins. The C9 to C28 stream is sent to a separate linear selective cracking unit to crack the C14+ paraffins; the cracked paraffins are separated (by fractionation, distillations, and the like) into a first stream comprising the C9 to C14 normal and lightly branched paraffins, a second stream comprising C14+(i.e., containing carbon chains from C15 to C28) paraffins, and a third stream comprising isoparaffins. The C9 to C14 paraffins from the linear selective cracking unit are isomerized to produce C9 to C14 mono-methyl paraffins. Contaminants, including but not limited to, comprise sulfur compounds, or nitrogen compounds, or phosphorous compounds, or oxygenates, or aromatics or combinations thereof, are removed from the isomerized C9 to C14 stream. The decontaminated stream is dehydrogenated to form olefins, di-olefins, and aromatics. The di-olefins are selectively hydrogenated to form additional olefins, and the aromatics are separated and removed forming an aromatics stream comprising the aromatics and a mono-olefin stream comprising the mono-olefins. Benzene is alkylated with the olefins, and the alkylation effluent comprises alkylbenzenes and benzene. The alkylbenzenes are then isolated.

The linear selective cracking and isomerization steps will be further described. The linear selective cracking takes place in a separate unit, rather than in the bottom bed of a first stage hydrocracking reactor because sulfur and nitrogen contaminants from the first stage can poison a metal-based hydrocracking catalyst. The C14+ paraffins are selectively cracked over the C9 to C14 due to higher absorption energy.

Selection of particular metal catalysts, including noble metals (such as ruthenium and platinum), and nickel can produce a much higher yield of normal paraffins with 9-14 carbons than previous processes. Suitable catalysts include, but are not limited to, $Ru/ZrO_2$, a $Pt—Al_2O_3$, Ni-alumina, or a $NiO_x$/clay. With these catalysts, the C14+ stream is able to generate linear cracking products without significant amounts of branched isomer production.

Of the preferred catalysts, the Ru catalyst exhibits much higher activity and per-pass nC9 to nC14 yield than the other catalysts. Under the optimized reaction conditions, it also produces very small amounts of methane and isomerized product. This has been found to be the best catalyst for such chemical transformation process. The $Pt—Al_2O_3$ catalyst can produce even lower methane yield than the Ru based catalyst with slightly less linear product yield.

The linear selective cracking conditions comprise temperatures in a range of 290° C. to 455° C., or pressures in a range of 2.8 MPa to 17.5 MPa, or combinations thereof.

The first stream comprising C9 to C14 paraffins from the linear selective cracking unit is isomerized to produce C9 to (C14 mono-methyl paraffins. The weight ratio of mono-methyl paraffins to normal paraffins in the isomerized stream is in the range of 3 to 60.

The isomerization catalyst comprises a zeolite comprising a 10-ring AEL framework or combinations thereof. The isomerization conditions comprise a temperature in a range of 280° C. to 400° C., or a pressure in a range of 2.8 MPa to 17.5 MPa, or combinations thereof.

The overall process will now be described in more detail.

To limit catalyst deactivation, the feed is treated to remove sulfur contamination before hydrodeoxygenation. Otherwise, sulfur accumulates on the catalyst and leads to deactivation. A high temperature hydrogen treatment was shown to recover some of the lost activity. The degree of hydrodeoxygenation can affect the selectivity to each of the normal paraffins in the 9 to 14 carbon range, A large degree of hydrodeoxygenation can bias the hydrodeoxygenated composition largely in favor of normal dodecane and normal decane to the detriment of normal undecane and normal tridecane. A small degree of hydrodeoxygenation can bias the hydrodeoxygenated composition in favor of normal undecane and normal tridecane to the detriment of normal dodecane and normal decane.

The hydrodeoxygenation reactor temperatures are kept low, less than 343° C. (650° F.) for typical biorenewable feedstocks and less than 304° C. (580° F.) for feedstocks with higher free fatty acid (FFA) concentration to avoid polymerization of olefins found in FFA. Generally, hydrodeoxygenation reactor pressure of about 700 kPa (100 psig) to about 21 MPa (3000 psig) are suitable.

The linearity of the alkylbenzene product is mostly dependent on the linearity of the paraffins used to alkylate the benzene. It is a common rule of thumb by those skilled in the art that the linearity of a paraffin feed drops by about 5-7 mass % after dehydrogenation and alkylation. Therefore, paraffin with 97 mass % linearity (or alternatively 3 mass % isoparaffin) would result in an alkylbenzene product with linearity around 90-92 mass %. This sets the requirement for paraffin linearity about 5-7 mass % higher than the specification for the alkylbenzene product. Typically the linearity of the paraffin product is measured by UOP 621, UOP411, or UOP732 standard test method available from ASTM, which is hereby incorporated by reference in its entirety. Linear alkylbenzenes may be analyzed using ASTM Standard Test Method D4337 hereby incorporated by reference in its entirety.

In FIG. 1, an exemplary system 100 for producing an alkylbenzene product from a specific triglyceride feed is illustrated.

In the illustrated embodiment, the selected natural oil feed 105 is delivered to a deoxygenation unit 110 which also receives a hydrogen feed (not shown). In the deoxygenation unit 110, the fatty acids in the natural oil feed 105 are deoxygenated and converted into normal paraffins. When the natural oil comprises triglycerides, the triglycerides are formed by three, typically different, fatty acid molecules that are bonded together with a glycerol bridge. The glycerol molecule includes three hydroxyl groups (HO—) and each fatty acid molecule has a carboxyl group (COOH). In triglycerides, the hydroxyl groups of the glycerol join the carboxyl groups of the fatty acids to form ester bonds. Therefore, during deoxygenation, the fatty acids are freed from the triglyceride structure and are converted into normal paraffins. The glycerol is converted into propane, and the oxygen in the hydroxyl and carboxyl groups is converted into water, carbon dioxide, or carbon monoxide. The deoxygenation reaction for fatty acids and triglycerides are respectively illustrated as:

$$H_2 + R—COOH \longrightarrow R + H_2O + CO_2$$

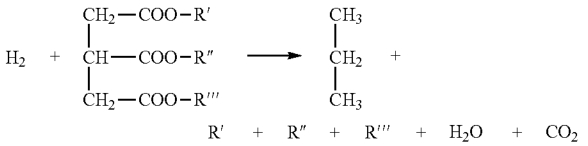

During the deoxygenation reaction, the length of a paraffin chain R″ created will vary by a value of one depending on the exact reaction pathway. It is understood that deoxygenation includes at least one of hydrodeoxygenation, decarboxylation, and decarbonylation, or any combination thereof. For instance, if carbon dioxide is formed, then the chain will have one fewer carbon than the fatty acid source. If water is formed, then the chain will match the length of the fatty acid source.

Operating conditions for the deoxygenating unit include pressures in the range of from about 250 to about 800 psig (about 1724 to about 5516 kPa) and temperatures in the range of from about 274° C. to about 371° C. (about 525° F. to about 700° F.) in one embodiment, from about 274° C. to about 338° C. (about 525° F. to about 640° F.) in another embodiment and from about 274° C. to about 310° C. (about 525° F. to about 590° F.) in another embodiment. Catalysts may include those containing one or more of Ni, Mo, Co, P, such as Ni—Mo, Ni—Mo—P, Ni—Co—Mo, or Co—Mo, on aluminas, silica, titania, zirconia, and mixtures thereof. Suitable hydrogen to hydrocarbon mole ratios include from about 1500 to 10,000, from about 4000 to 9000, and from about 5000-8000 standard cubic feet per barrel of feedstock (scf/B). Suitable space velocities include 0.2-3.0 $hr^{-1}$ LHSV. Conditions are selected to minimize cracking or isomerizing the paraffins.

The deoxygenated product contains normal paraffins, water, carbon dioxide, carbon monoxide, and propane.

The C9 to C28 stream 115 from the deoxygenation unit 110 is sent to the linear selective cracking unit 120 where it is selectively cracked to form a first stream 125 comprising normal or lightly branched C9 to C14 paraffins, a second stream 130 comprising C14+ paraffins 135, an a third stream comprising isoparaffins, as described above.

The first stream 125 is sent to the isomerization unit 140 where a portion of the C9 to C14 paraffins are converted to mono-methyl paraffins. The isomerization catalyst comprises a zeolite comprising a 10-ring AEL framework or combinations thereof. Suitable isomerization catalysts include, but are not limited to, SAPO-11, AEI, AEL, AFO, AFX, ATO, BEA, CHA, FAU, FER, MEL, MF, MOR, MRE, MTT, MWW or TON topology such as EU-2, ZSM-11, ZSM-22, ZSM-23, ZSM-48, SAPO-5, SAPO-11, SAPO-31, SAPO-34, SAPO-41, SSZ-13, SSZ-16, SSZ-39, MCM-22, zeolite Y, ferrierite mordenite, ZSM-5 or zeolite beta, and combinations thereof.

The isomerization conditions comprise a temperature in a range of 280° C. to 400° C., or a pressure in a range of 2.8 MPa to 17.5 MPa, 1500-10000 standard cubic foot of hydrogen per barrel of feed, 0.25-2.5 LHSV or combinations thereof.

The overall process will now be described in more detail.

The isomerized stream 145 from the isomerization unit 140 is sent to a decontamination unit 150. The decontamination unit 150 removes contaminants in an adsorption system from the C9 to C14 mono-methyl paraffins in the isomerized stream 145. The contaminants include, but are not limited to, sulfur compounds, or nitrogen compounds, or phosphorous compounds, or oxygenates, or aromatics or combinations thereof.

The decontaminated stream 155 is sent to a dehydrogenation unit 160 where hydrogen is removed to produce a dehydrogenated stream 165 comprising mono-olefins, di-olefins, and aromatics. In the dehydrogenation unit 160, the paraffins are dehydrogenated into mono-olefins of the same carbon numbers as the paraffins. Typically, dehydrogenation occurs through known catalytic processes, such as the commercially popular Pacol process. Di-olefins (i.e., dienes) and aromatics are also produced as an undesired result of the dehydrogenation reactions as expressed in the following equations:

$$C_xH_{2x+2} \rightarrow C_xH_{2x}+H_2 \quad \text{Mono-olefin formation:}$$

$$C_xH_{2x} \rightarrow C_xH_{2x+2}+H_2 \quad \text{Di-olefin formation:}$$

$$C_xH_{2x-2} \rightarrow C_xH_{2x-6}+2H_2 \quad \text{Aromatic formation:}$$

Operating conditions for the dehydrogenation unit 160 include space velocities from about 5 to about 50 LHSV and from about 20 to about 32 LHSV; pressures from about 34 kPa (g) to about 345 kPa (g) (about 5 psig to about 50 psig) and from about 103 kPa (g) to about 172 kPa (g) (about 15 psig to about 25 psig); temperatures from about 400° C. to about 500° C. and from about 440° C. to about 490° C., and hydrogen to hydrocarbon mole ratios from about 1-12 and from about 3-7. An example of a suitable catalyst is a Pt on alumina catalyst where platinum is attenuated with an attenuator metal. Another suitable catalyst is described in U.S. Pat. No. 6,177,381 hereby incorporated by reference in its entirety. The dehydrogenation unit 160 may be operated dry or with water injection up to about 2000 mass-ppm water. Hydrogen can be recycled to the deoxygenation unit upstream.

The dehydrogenated stream 165 is sent to a selective hydrogenation unit 170, such as a DeFine reactor, where at least a portion of the di-olefins are hydrogenated to form additional mono-olefins. As a result, the mono-olefin stream 175 has an increased mono-olefin concentration compared to the dehydrogenated stream 165. The aromatics are separated and removed as aromatics stream 180. A light end stream 1185 containing any lights, such as butane, propane, ethane and methane, that resulted from cracking or other reactions during upstream processing can also removed.

The mono-olefin stream 175 comprising mono-olefins is sent to the alkylation unit 190 along with a benzene stream 195. The benzene is alkylated with the mono-olefins to form alkylbenzene. The alkylation unit 190 contains a catalyst, such as a solid acid catalyst, that supports alkylation of the benzene with the mono-olefins. Fluorinated silica-alumina, hydrogen fluoride (HF), aluminum chloride ($AlCl_3$), zeolitic, and ionic liquid catalysts are examples of major catalysts in commercial use for the alkylation of benzene with linear mono-olefins and may be used in the alkylation unit 190. As a result of alkylation, alkylbenzene, typically called linear alkylbenzene (LAB), is formed according to the reaction:

$$C_6H_6+C_xH_{2x} \rightarrow C_6H_5C_xH_{2x+1}$$

Suitable operating conditions for the alkylation unit 190 include space velocities from 1 to about 10 LHSV, pressures to maintain liquid phase operation, such as about 2068 kPa (g) to about 4137 kPa (g) (about 300 psig to about 600 psig), temperatures in the range of from about 80° C. to about 180° C. and 120° C. to about 170° C., benzene to olefin mole ratios of about 3 to about 40 and about 8 to about 35.

Surplus amounts of benzene are supplied to the alkylation unit 190 to achieve high degree of desired alkylation. Therefore, the alkylation effluent 200 exiting the alkylation unit 190 contains alkylbenzene and unreacted benzene. Further, the alkylation effluent 200 may also include some unreacted paraffins. The alkylation effluent 200 is passed to a benzene separation unit 205, such as a fractionation column, for separating the unreacted benzene and paraffins from the alkylation effluent 200. The unreacted benzene exits the benzene separation unit 205 in a benzene recycle stream 210 that may be sent back into the alkylation unit 190 to maintain the desired benzene/olefin ratio (e.g., 1-50) and to reduce the volume of fresh benzene needed. The fresh benzene requirement (i.e., the net benzene) is determined by the net olefin to the alkylation unit. A paraffin stream 215 can also be separated out and recycled to the dehydrogenation unit 160.

As a result of the post-alkylation separation processes, the linear alkylbenzene product 220 is isolated. It is noted that such separation processes are not necessary in all embodiments in order to isolate the linear alkylbenzene product 220.

The linear alkylbenzene product 220 is a linear alkylbenzene product comprising: alkylbenzenes having the formula $C_6H_5C_nH_{2n+1}$ wherein n is from 9 to 14. In some embodiments, at least 80 mass % of the alkylbenzenes have linear alkyl groups, or at least 90 mass %.

The linear alkylbenzene may be sulfonated to provide a linear alkylbenzene sulfonate product comprising: alkylbenzene sulfonate compounds having the formula $C_nH_{2n+1}C_6H_4SO_3H$ wherein n is from 10 to 14, or wherein n is from 11 to 13.

In some embodiments, either before or after the decontamination step, the isomerized stream (if before the decontamination step) or the decontaminated stream (if after the decontamination step) can be separated in an absorption separation system (not shown) in which the mono-methyl paraffins are preferentially absorbed by the absorbent and the non-mono-methyl paraffins remain in the fluid phase. In some embodiments, the absorbent in the absorption separation system is divided into a plurality of absorbent beds.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Unless indicated otherwise, overhead lines and bottoms lines refer to the net lines from the column downstream of any reflux or reboil take-off to the column. Stripper columns may omit a reboiler at a bottom of the column and instead provide heating requirements and separation impetus from a fluidized inert media such as steam.

As used herein, the term "a component-rich stream" or "a component stream" means that the stream coming out of a vessel has a greater concentration of the component than the feed to the vessel. As used herein, the term "a component-lean stream" means that the lean stream coming out of a vessel has a smaller concentration of the component than the feed to the vessel.

EXAMPLES

Example 1

A coconut oil feed was deoxygenated, to form paraffins, dehydrogenated to form mono-olefins, and benzene was alkylated with the mono-olefins to form an alkylbenzene product with a modern carbon content of 62 mass 96 modern carbon as determined by ASTM D6866 as compared to a theoretical modern carbon content of 66.4 mass %, a bromine number of 1 g Br/per gram sample as determined by UOP standard test method 304, and a linearity of 92 mass %.

Example 2

Figure 2:
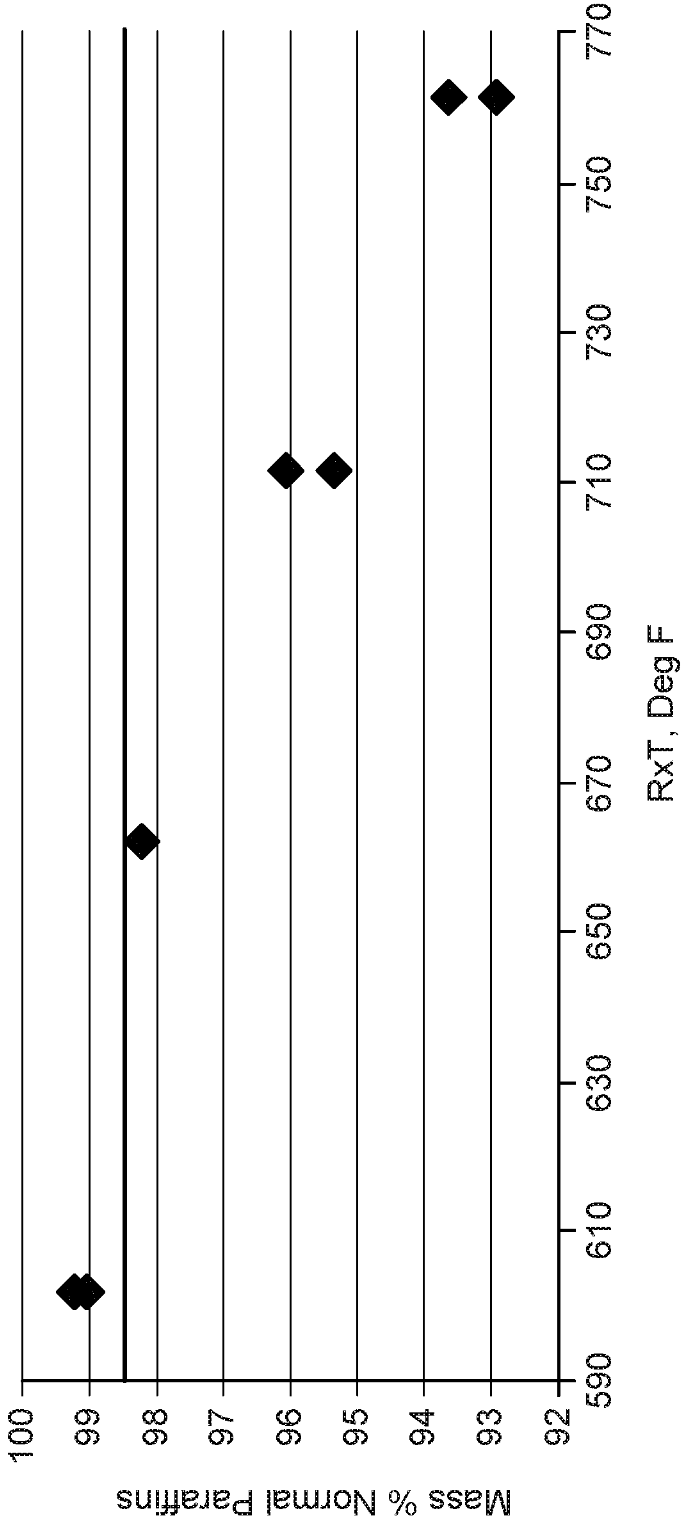
FIG. 2 is a plot of the mass-% normal paraffins versus deoxygenation temperature in accordance with Example 2.

An oil was deoxygenated using a catalyst at a pressure of 480 psig, H, to bio-oil ratio of 7200 scf/B and a LHSV of 1 hr'. During operation, the deoxygenation reaction temperature was increased in steps from 315° C. (600° F.) to 34.9° C. (660° F.) and then to 377° C. (710° F.) and 404° C. (760° F.) to monitor the response of linearity in the final product to reaction temperature. The results are shown in FIG. 2 which is a plot of the concentration in mass % of normal C10-C 13 paraffins versus reaction temperature. FIG. 2 clearly demonstrates that as the deoxygenation reaction temperature is increased, the concentration of linear paraffins decreases. Controlling the temperature to less than 404° C. (760° F.) resulted in greater than 92 mass percent linear paraffins.

Note: Examples 1 and 2 were previously included in U.S. Pat. No. 9,079,814 as Examples 3 and 4.

SPECIFIC EMBODIMENTS

While the following is described in conjunction with specific embodiments, it will be understood that this description is intended to illustrate and not limit the scope of the preceding description and the appended claims.

A first embodiment of the invention is a method for production of a mono methyl alkylbenzene product from a natural oil comprising deoxygenating the natural oil to form a paraffin stream comprising C9 to C28 carbon chains; linear selective cracking the paraffin stream in a separate linear selective cracking unit under linear selective cracking conditions in the presence of a linear selective cracking catalyst to form a first stream comprising normal or lightly branched C9 to C14 paraffins, a second stream comprising C14+ paraffins, and a third stream comprising iso paraffins; isomerizing the first stream under isomerization conditions in the presence of an isomerization catalyst to form an isomerized stream comprising C9 to C14 mono-methyl paraffins, wherein the isomerization catalyst comprises a zeolite comprising a 10-ring AEL framework or combinations thereof; removing contaminants from the isomerized stream to form a decontaminated stream wherein the contaminates comprise sulfur compounds, or nitrogen compounds, or phosphorous compounds, or oxygenates, or aromatics, or combinations thereof; dehydrogenating the decontaminated stream to provide a dehydrogenated stream comprising mono-olefins, di-olefins, and aromatics; selectively hydrogenating the di-olefins in the dehydrogenated stream to form additional mono-olefins, and separating and removing the aromatics from the mono-olefins to form an aromatics stream comprising the aromatics and a mono-olefins stream comprising the mono-olefins alkylating benzene with the mono-olefins under alkylation conditions to provide an alkylation effluent comprising alkylbenzenes and benzene; and isolating the alkylbenzenes to provide the alkylbenzene product derived from the natural oil. An embodiment of the invention is one, any or all of prior embodiments in this paragraph up through the first embodiment in this paragraph further comprising separating the isomerized stream through a first absorption separation system, wherein the mono methyl paraffins in the mixture are preferentially adsorbed by a first adsorbent and where the non-mono methyl paraffins remain in the fluid phase, before removing the contaminants from the isomerized stream; or separating the decontaminated stream through a second absorption separation system, wherein the mono methyl paraffins in the mixture are preferentially adsorbed by a second adsorbent and where the non-mono methyl paraffins remain in the fluid phase, before dehydrogenating the decontaminated stream. An embodiment of the invention is one, any or all of prior embodiments in this paragraph up through the first embodiment in this paragraph wherein the adsorbent in the first absorption separation system is divided into a plurality of adsorbent bed zones; or wherein the adsorbent in the second absorption separation system is divided into a plurality of adsorbent bed zones; or both. An embodiment of the invention is one, any or all of prior embodiments in this paragraph up through the first embodiment in this paragraph wherein the isomerized stream comprises a weight ratio of mono-methyl paraffins to normal paraffins of 3 to 60. An embodiment of the invention is one, any or all of prior embodiments in this paragraph up through the first embodiment in this paragraph further comprising recycling the second stream comprising C14+ paraffins to the linear selective cracking unit. An embodiment of the invention is one, any or all of prior embodiments in this paragraph up through the first embodiment in this paragraph wherein the linear selective cracking catalyst comprises a ruthenium, or a platinum, or a nickel supported catalyst, or mixtures thereof. An embodiment of the invention is one, any or all of prior embodiments in this paragraph up through the first embodiment in this paragraph wherein the linear selective cracking conditions comprise a temperature in a range of 290° C. to 455° C., or a pressure in a range of 2.8 MPa to 17.5 MPa, or 1500-10000 standard cubic foot of hydrogen per barrel of feed, or 0.25-2.5 L HSV, or combinations thereof. An embodiment of the invention is one, any or all of prior embodiments in this paragraph up through the first embodiment in this paragraph wherein the isomerization conditions comprise a temperature in a range of 280° C. to 400° C., or a pressure in a range of 2.8 MPa to 17.5 MPa, or 1500-10000 Scfb hydrogen feed, 0.25-2.5 LHSV. or combinations thereof. An embodiment of the invention is one, any or all of prior embodiments in this paragraph up through the first embodiment in this paragraph wherein the zeolite comprising a 10-ring AEL framework comprises SAPO-11. An embodiment of the invention is one, any or all of prior embodiments in this paragraph up through the first embodiment in this paragraph wherein the isomerization catalyst comprises of platinum or nickel tungsten sulfide. An embodiment of the invention is one, any or all of prior embodiments in this paragraph up through the first embodiment in this paragraph 2 wherein the first adsorbent comprises a ZSM or a type X zeolite.

A second embodiment of the invention is a method for production of a mon-methyl alkylbenzene product from a natural oil comprising deoxygenating the natural oil to form a paraffin stream comprising C9 to C28 carbon chains; linear selective cracking the paraffin stream in a separate linear selective cracking unit under linear selective cracking conditions in the presence of a linear selective cracking catalyst to form a first stream comprising normal or lightly branched C9 to C14 paraffins, a second stream comprising C14+ paraffins, and a third stream comprising iso paraffins; isomerizing the first stream under isomerization conditions in the presence of an isomerization catalyst to form an isomerized stream comprising C9 to C14 mono-methyl paraffins, wherein the isomerization catalyst comprises a zeolite comprising a 10-ring AEL framework or combinations thereof, removing contaminants from the isomerized stream to form a decontaminated stream wherein the contaminates comprise sulfur compounds, or nitrogen compounds, or phosphorous compounds, or oxygenates, or aromatics, or combinations thereof, dehydrogenating the decontaminated stream to provide a dehydrogenated stream comprising mono-olefins, di-olefins, and aromatics; selectively hydrogenating the di-olefins in the dehydrogenated stream to form additional mono-olefins, and separating and removing the aromatics from the mono-olefins to form an aromatics stream comprising the aromatics and a mono-olefins stream comprising the mono-olefins alkylating benzene with the mono-olefins under alkylation conditions to provide an alkylation effluent comprising alkylbenzenes and benzene; isolating the alkylbenzenes to provide the alkylbenzene product derived from the natural oil; and separating the isomerized stream through a first absorption separation system, wherein the mono methyl paraffins in the mixture are preferentially adsorbed by the adsorbent and where the non-mono methyl paraffins remain in the fluid phase before removing the contaminants from the isomerized stream, wherein the adsorbent in the first absorption separation system is divided into a plurality of adsorbent bed zones; or separating the decontaminated stream through a second absorption separation system, wherein the mono methyl paraffins in the mixture are preferentially adsorbed by the adsorbent and where the non-mono methyl paraffins remain in the fluid phase before dehydrogenating the decontaminated stream, wherein the adsorbent in the second absorption separation system is divided into a plurality of adsorbent bed zones. An embodiment of the invention is one, any or all of prior embodiments in this paragraph up through the second embodiment in this paragraph wherein the isomerized stream comprises a weight ratio of mono-methyl paraffins to normal paraffins of 3 to 60. An embodiment of the invention is one, any or all of prior embodiments in this paragraph up through the second embodiment in this paragraph further comprising recycling the second stream comprising C14+ paraffins to the linear selective cracking unit. An embodiment of the invention is one, any or all of prior embodiments in this paragraph up through the second embodiment in this paragraph wherein the linear selective cracking catalyst comprises a ruthenium, or a platinum, or a nickel supported catalyst, or mixtures thereof. An embodiment of the invention is one, any or all of prior embodiments in this paragraph up through the second embodiment in this paragraph wherein the linear selective cracking conditions comprise a temperature in a range of 290° C. to 455° C., or a pressure in a range of 2.8 MPa to 17.5 MPa, or 1500-10000 standard cubic foot of hydrogen per barrel of feed, 0.25-2.5 LHSV, or combinations thereof. An embodiment of the invention is one, any or all of prior embodiments in this paragraph up through the second embodiment in this paragraph wherein the isomerization conditions comprise a temperature in a range of 280° C. to 400° C., or a pressure in a range of 2.8 MPa to 17.5 MPa, or combinations thereof. An embodiment of the invention is one, any or all of prior embodiments in this paragraph up through the second embodiment in this paragraph wherein the zeolite comprising a 10-ring AEL framework comprises SAPO-11. An embodiment of the invention is one, any or all of prior embodiments in this paragraph up through the second embodiment in this paragraph wherein the first adsorbent comprises a ZSM or a type X zeolite.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A method for production of a mono methyl alkyl benzene product from a natural oil comprising:

deoxygenating the natural oil to form a paraffin stream comprising C9 to C28 carbon chains;

linear selective cracking the paraffin stream in a separate linear selective cracking unit under linear selective cracking conditions in the presence of a linear selective cracking catalyst to form a first stream comprising normal or lightly branched C9 to C14 paraffins, a second stream comprising C14+ paraffins, and a third stream comprising iso paraffins;

isomerizing the first stream under isomerization conditions in the presence of an isomerization catalyst to form an isomerized stream comprising C9 to C14 mono-methyl paraffins, wherein the isomerization catalyst comprises one or more zeolites comprising a 10-ring AEL framework;

removing contaminants from the isomerized stream to form a decontaminated stream wherein the contaminants comprise sulfur compounds, or nitrogen compounds, or phosphorous compounds, or oxygenates, or aromatics, or combinations thereof;

dehydrogenating the decontaminated stream to provide a dehydrogenated stream comprising mono-olefins, di-olefins, and aromatics;

selectively hydrogenating the di-olefins in the dehydrogenated stream to form additional mono-olefins, and separating and removing the aromatics from the mono-olefins to form an aromatics stream comprising the aromatics and a mono-olefins stream comprising the mono-olefins;

alkylating benzene with the mono-olefins under alkylation conditions to provide an alkylation effluent comprising alkylbenzenes and benzene; and isolating the alkylbenzenes to provide the alkylbenzene product derived from the natural oil.

2. The method of claim 1 further comprising:

separating the isomerized stream through a first absorption separation system, wherein the mono methyl paraffins in the mixture are preferentially adsorbed by a first adsorbent and where the non-mono methyl paraffins remain in the fluid phase, before removing the contaminants from the isomerized stream;

or separating the decontaminated stream through a second absorption separation system, wherein the mono methyl paraffins in the mixture are preferentially adsorbed by a second adsorbent and where the non-mono methyl paraffins remain in the fluid phase, before dehydrogenating the decontaminated stream.

3. The method of claim 2:

wherein the adsorbent in the first absorption separation system is divided into a plurality of adsorbent bed zones; or wherein the adsorbent in the second absorption separation system is divided into a plurality of adsorbent bed zones;

or both.

4. The method of claim 2 wherein the first adsorbent comprises a ZSM or a type X zeolite.

5. The method of claim 1 wherein the isomerized stream comprises a weight ratio of mono-methyl paraffins to normal paraffins of 3 to 60.

6. The method of claim 1 further comprising:

recycling the second stream comprising C14+ paraffins to the linear selective cracking unit.

7. The method of claim 1 wherein the linear selective cracking catalyst comprises a ruthenium, or a platinum, or a nickel supported catalyst, or mixtures thereof.

8. The method of claim 1 wherein the linear selective cracking conditions comprise a temperature in a range of 290° C. to 455° C., or a pressure in a range of 2.8 MPa to 17.5 MPa, or combinations thereof.

9. The method of claim 1 wherein the isomerization conditions comprise a temperature in a range of 280° C. to 400° C., or a pressure in a range of 2.8 MPa to 17.5 MPa, or 1500-10000 standard cubic foot of hydrogen per barrel of feed, or 0.25-2.5 LHSV, or combinations thereof.

10. The method of claim 1 wherein the one or more zeolites comprising a 10-ring AEL framework comprises SAPO-11.

11. The method of claim 1 wherein the isomerization catalyst comprises platinum or nickel tungsten sulfide.

12. A method for production of a mono-methyl alkyl benzene product from a natural oil comprising:

deoxygenating the natural oil to form a paraffin stream comprising C9 to C28 carbon chains;

linear selective cracking the paraffin stream in a separate linear selective cracking unit under linear selective cracking conditions in the presence of a linear selective cracking catalyst to form a first stream comprising normal or lightly branched C9 to C14 paraffins, a second stream comprising C14+ paraffins, and a third stream comprising iso paraffins;

isomerizing the first stream under isomerization conditions in the presence of an isomerization catalyst to form an isomerized stream comprising C9 to C14 mono-methyl paraffins, wherein the isomerization catalyst comprises one or more zeolites comprising a 10-ring AEL framework;

removing contaminants from the isomerized stream to form a decontaminated stream wherein the contaminants comprise sulfur compounds, or nitrogen compounds, or phosphorous compounds, or oxygenates, or aromatics, or combinations thereof;

dehydrogenating the decontaminated stream to provide a dehydrogenated stream comprising mono-olefins, di-olefins, and aromatics;

selectively hydrogenating the di-olefins in the dehydrogenated stream to form additional mono-olefins, and separating and removing the aromatics from the mono-olefins to form an aromatics stream comprising the aromatics and a mono-olefins stream comprising the mono-olefins:

alkylating benzene with the mono-olefins under alkylation conditions to provide an alkylation effluent comprising alkylbenzenes and benzene;

isolating the alkyl benzenes to provide the alkylbenzene product derived from the natural oil; and separating the isomerized stream through a first absorption separation system, wherein the mono methyl paraffins in the mixture are preferentially adsorbed by the adsorbent and where the non-mono methyl paraffins remain in the fluid phase before removing the contaminants from the isomerized stream, wherein the adsorbent in the first absorption separation system is divided into a plurality of adsorbent bed zones;

or separating the decontaminated stream through a second absorption separation system, wherein the mono methyl paraffins in the mixture are preferentially adsorbed by the adsorbent and where the non-mono methyl paraffins remain in the fluid phase before dehydrogenating the decontaminated stream, wherein the adsorbent in the second absorption separation system is divided into a plurality of adsorbent bed zones.

13. The method of claim 12 wherein the isomerized stream comprises a weight ratio of mono-methyl paraffins to normal paraffins of 3 to 60.

14. The method of claim 12 further comprising:

recycling the second stream comprising C14+ paraffins to the linear selective cracking unit.

15. The method of claim 12 wherein the linear selective cracking catalyst comprises a ruthenium, or a platinum, or a nickel supported catalyst, or mixtures thereof.

16. The method of claim 12 wherein the linear selective cracking conditions comprise a temperature in a range of 290° C. to 455° C., or a pressure in a range of 2.8 MPa to 17.5 MPa, or combinations thereof.

17. The method of claim 12 wherein the isomerization conditions comprise a temperature in a range of 280° C. to 400° C., or a pressure in a range of 2.8 MPa to 17.5 MPa, or 1500-10000 standard cubic foot of hydrogen per barrel of feed, 0.25-2.5 LHSV, or combinations thereof.

18. The method of claim 12 wherein the one or more zeolites comprising a 10-ring AEL framework comprises SAPO-11.

19. The method of claim 12 wherein the first adsorbent comprises a ZSM or a type X zeolite.

* * * * *